US008658427B2

(12) United States Patent
van Ravenzwaay et al.

(10) Patent No.: US 8,658,427 B2
(45) Date of Patent: Feb. 25, 2014

(54) MEANS AND METHODS FOR ASSESSING INCREASED PEROXISOMAL PROLIFERATION

(75) Inventors: Bennard van Ravenzwaay, Altrip (DE); Werner Mellert, Haβloch (DE); Eric Fabian, Ludwigshafen (DE); Volker Strauss, Bad Dürkheim (DE); Tilmann B. Walk, Kleinmachnow (DE); Ralf Looser, Berlin (DE); Edgar Leibold, Carlsberg (DE); Hennicke Kamp, Bischheim (DE); Georgia Coelho Palermo Cunha, Sao Paulo (BR); Michael Manfred Herold, Berlin (DE); Jan C Wiemer, Berlin (DE); Alexandre Prokoudine, Berlin (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/994,705

(22) PCT Filed: May 26, 2009

(86) PCT No.: PCT/EP2009/056386
§ 371 (c)(1),
(2), (4) Date: Feb. 11, 2011

(87) PCT Pub. No.: WO2009/153139
PCT Pub. Date: Dec. 23, 2009

(65) Prior Publication Data
US 2011/0129933 A1 Jun. 2, 2011

(30) Foreign Application Priority Data
May 28, 2008 (EP) .................................... 08157118
Jan. 28, 2009 (EP) .................................... 09151549

(51) Int. Cl.
*G01N 33/92* (2006.01)
*G01N 33/68* (2006.01)

(52) U.S. Cl.
USPC .................. 436/71; 436/63; 436/86; 436/89; 436/161; 436/173

(58) Field of Classification Search
USPC ............ 436/63, 71, 86, 89, 161, 173; 435/29, 435/39; 250/281, 282
See application file for complete search history.

(56) References Cited

U.S. PATENT DOCUMENTS

| 4,540,884 A | 9/1985 | Stafford et al. |
| 5,397,894 A | 3/1995 | Wells et al. |
| 2005/0009005 A1 | 1/2005 | Watkins |
| 2005/0059096 A1* | 3/2005 | Pruimboom-Brees et al. ............... 435/7.2 |
| 2007/0265216 A1 | 11/2007 | Gross et al. |
| 2008/0176266 A1 | 7/2008 | Berger et al. |
| 2011/0172926 A1* | 7/2011 | Watkins .................. 702/19 |

FOREIGN PATENT DOCUMENTS

| WO | WO-2007/014825 A1 | 2/2007 |
| WO | WO-2007/110357 A2 | 10/2007 |
| WO | WO-2007/110358 A2 | 10/2007 |

OTHER PUBLICATIONS

Reddy, et al., "Carcinogenesis by Hepatic Peroxisome Proliferators: Evaluation of the Risk of Hypolipidemic Drugs and Industrial Plasticizers to Humans", *Critical Reviews in Toxicology*, vol. 12, Issue 1, pp. 1-58 (1983).

Moody, et al., "Peroxisome Proliferation and Nongenotoxic Carcinogenesis: Commentary on a Symposium", *Fundamental and Applied Toxicology*, vol. 16, pp. 233-248 (1991).

Youssef et al., "Extraperoxisomal Targets of Peroxisome Proliferators: Mitochondrial, Microsomal, and Cytosolic Effects. Implications for Health and Disease" *Critical Reviews in Toxicology*, vol. 28, No. 1, pp. 1-33 (1998).

Nissen, "Liquid chromatography-mass spectrometry. General principles and instrumentation", *Journal of Chromatography A*, vol. 703, pp. 37-57 (1995).

Xu et al., "Effects of di-(2-ethylhexyl)-phthalate and its metabolites on the lipid profiling in rat HRP-1 trophoblast cells", *Archives of Toxicology*, vol. 80, No. 5, pp. 293-298 (2006).

"Analysis of fatty acids in rat liver peroxisomes", Database: CAPLUS, Accession No. 2001:772623 (2001).

Curstedt et al: "Individual Molecular Species of Phosphatidyl Cholines and Phosphatidylinositols in Liver of Rats Fed Bis-(2 Ethylhexyl) Phthalate" *Medical Biology*, vol. 61, No. 4, pp. 219-222 (1983).

Vazquez et al: "Gemfibrozil modifies acyl composition of liver microsomal phospholipids from guinea-pigs without promoting peroxisomal proliferation", *Biochemical Pharmacology*, vol. 46, No. 8, pp. 1515-1518 (1993).

(Continued)

*Primary Examiner* — Maureen Wallenhorst
(74) *Attorney, Agent, or Firm* — Devesh Srivastava

(57) ABSTRACT

The present invention pertains to the field of toxicological assessments of risk stratification of chemical compounds. Specifically, it relates to a method for diagnosing increased peroxisomal proliferation. It also relates to a method of determining whether a compound is capable of inducing such peroxisomal proliferation in a subject and to a method of identifying a drug for treating increased peroxisomal proliferation. Furthermore, the present invention relates to a data collection of characteristic values of at least five metabolites, a data storage medium for the data collection, and a system and a device for diagnosing increased peroxisomal proliferation. Finally, the present invention pertains to the use of a group of metabolites or means for the determination thereof for the manufacture of a diagnostic device or composition for diagnosing increased peroxisomal proliferation in a subject.

17 Claims, 2 Drawing Sheets

(56) References Cited

OTHER PUBLICATIONS

Eveillard et al.; "Identification of potential mechanisms of toxicity after di-(2-ethylhexyl)-phthalate (DEHP) adult exposure in the liver using a systems biology approach", *Toxicology and Applied Pharmacology*, vol. 236, No. 3, pp. 282-292 (2009).
Deluca, "Direct Analysis of Bacterial Fatty Acids by Curie-Point Pyrolysis Tandem Mass Spectrometry", *Analytical Chemistry*, vol. 62, No. 14, pp. 1465-1472 (1990).
Dunn et al., "Metabolic profiling of serum using Ultra Performance Liquid Chromatography and the LTQ-Orbitrap mass spectrometry system", *Journal of Chromatography B*, vol. 871, No. 2, pp. 288-298 (2008).
Tououl et al.: "Lipid imaging by gold cluster time-of-flight secondary ion mass spectrometry: application to Duchenne muscular dystrophy", *Journal of Lipid Research*, vol. 46, No. 7, pp. 1388-1395 (2005).
Zhen et al, "Metabolomic and Genetic Analysis of Biomarkers for Peroxisome Proliferator-Activated Receptor α Expression and Activation", *Molecular Endocrinology*, vol. 21, No. 9, pp. 2136-2151 (2007).
Thorne et al., "Clofibrate and other peroxisomal proliferating agents relatively specifically inhibit synthesis of ethanolamine phosphoglycerides in cultured human fibroblasts", *Biochimica et Biophysica Acta*, vol. 1214, No. 2, pp. 161-170 (1994).
Mortensen et al., "Dose-Related Decrease of Serum Coenzyme Q10 During Treatment with HMG-CoA Reductase Inhibitors", *Molec. Aspects Med.*, vol. 18, pp. s137-s144 (1997).
Nishimura, T., "Evaluation of Environmental Harmful Materials Measured by Peroxisome Proliferating Activities", Proceedings of Symposium on Toxicology and Environmental Health, 1999, vol. 25, p. 72.
Rao, M.S., "Dehydroepiandrosterone-Induced Peroxisome Proliferation in the Rat: Evaluation of Sex Differences", Proc. Soc. Exp. Biol. Med., 1994, vol. 207, No. 2, pp. 186-190.
Lake, Brian G., "Mechanisms of Hepatocarcinogenicity of Peroxisome-Proliferating Drugs and Chemicals", Ann. Rev. Pharmacol. Toxicol., 1995, vol. 35, pp. 483-507.
Vazquez, M., "Gemfibrozil modifies acyl composition of liver microsomal phospholipids from guinea-pigs without promoting peroxisomal proliferation", Biochemical Pharmacology, 1993, vol. 46, No. 8, pp. 1515-1518.

\* cited by examiner

MEANS AND METHODS FOR ASSESSING INCREASED PEROXISOMAL PROLIFERATION

RELATED APPLICATIONS

This application is a national stage application (under 35 U.S.C. §371) of PCT/EP2009/056386, filed May 26, 2009, which claims benefit of European Application No. 08157118.4, filed May 28, 2008, and European Application No. 09151549.4, filed Jan. 28, 2009.

The present invention pertains to the field of toxicological assessments for risk stratification of chemical compounds. Specifically, it relates to a method for diagnosing peroxisomal proliferation. It also relates to a method of determining whether a compound is capable of inducing such peroxisomal proliferation in a subject and to a method of identifying a drug for treating peroxisomal proliferation. Furthermore, the present invention relates to a data collection comprising characteristic values of at least five metabolites, a data storage medium comprising said data collection, and a system and a device for diagnosing peroxisomal proliferation. Finally, the present invention pertains to the use of a group of metabolites or means for the determination thereof for the manufacture of a diagnostic device or composition for diagnosing peroxisomal proliferation in a subject.

Peroxisomes are intracellular organelles of eukaryotic cells. Their enzymatic content varies across species. However, peroxisomes, in principle, contain enzymes for oxidative reactions, like the beta-oxidation of very-long-chain fatty acids. In this process, the fatty acids are broken down into two carbon units at a time, converted to Acetyl-CoA, which is then transported back to the cytosol for further use. In animal cells, beta-oxidation can also occur in the mitochondria while in yeast and plant cells, this process occurs exclusively in the peroxisomes. Moreover, in animals, the first steps in the formation of plasmalogen occur in peroxisomes. Plasmalogen is the most abundant phospholipid in myelin. Deficiency of plasmalogens causes profound abnormalities in the myelination of nerve cells and, thus, leads to diseases of the nervous system. Peroxisomes also play a role in the synthesis of bile acids and proteins. Impaired peroxisomal function leads to peroxisomal disorders, a class of medical conditions that lead to lipid metabolism diseases.

An increase in peroxisome numbers will lead to an increased formation of radical oxidative molecular species, such as reactive oxygen species (ROS), and, thus, to an increased oxidative stress for the cell. Accordingly, increased peroxisomal activity will elicit disorders caused by increased oxidative stress, such as damages on proteins, lipids or nucleic acids. Therefore, peroxisomal proliferation will increase the somatic mutagenesis rate as well as induce cell death by apoptosis or even necrosis. Additionally, a liver tumor promoting effect of peroxisome proliferators is discussed (Reddy, J. K. and Lalwani, N. D. (1983) Carcinogenesis by hepatic peroxisome proliferators: evaluation of the risk of hypolipidemic drugs and industrial plasticizers to humans. Crit Rev. Toxicol. 12, 1-58; Moody, D. E., Reddy, J. K., Lake, B. G., Popp, J. A. and Reese, D. H. (1991) Peroxisome proliferation and nongenotoxic carcinogenesis. Commentary on a symposium. Fundam. Appl. Toxicol. 16, 232-248).

Chemical compounds, such as phthalates, fenofibrate, or clofibrate, have been shown to induce peroxisomal proliferation. Such compounds are also called "peroxisomal proliferators". Moreover, due to their capability of inducing peroxisomal proliferation, and subsequent events (radical oxygen species formation and cell proliferation) these compounds also increase the risk for somatic mutations resulting in disease such as cancer or impaired metabolism (e.g. thyroid disorders, reproductive dysfunction, skeletal and cardiac myopathies, dysfunction of the immune system; Youssef, J. and Badr, M. (1998) Extraperoxisomal Targets of Peroxisome Proliferators: Mitochondrial, Microsomal, and Cytosolic Effects. Implications for Health and Disease. Crit. Rev. Toxicol. 28: 1-33).

Further, chemical compounds which are used in any kind of industry in the European Community, e.g., will now need to comply with REACH (Registration, Evaluation, and Authorisation of Chemicals). It will be understood that the potential of a chemical compound to induce peroxisomal proliferation will be deemed as a high risk for the compound and, consequently, the compound will be available only for limited applications and when obeying high security standards.

Sensitive and specific methods for assessing the capability of a compound to induce peroxisomal proliferation in an efficient and reliable manner, and to differentiate between said mode of action and other hepatotoxic effects are not yet available but would, nevertheless, be highly appreciated.

Thus, the technical problem underlying the present invention could be seen as the provision of means and methods for complying with the aforementioned needs. The technical problem is solved by the embodiments characterized in the claims and described herein below.

Accordingly, the present invention relates to a method for diagnosing increased peroxisomal proliferation comprising:
(a) determining the amount of at least one, preferably, at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline in a test sample of a male subject suspected to suffer from increased peroxisomal proliferation or at least one, preferably, at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6) in a test sample of a female subject suspected to suffer from increased peroxisomal proliferation, and
(b) comparing the amounts determined in step (a) to a reference, whereby increased peroxisomal proliferation is to be diagnosed.

The term "Phosphatidylcholine (C18:0/C22:6)" as used herein refers to molecular species, preferably, characterized by the sum parameter of glycerophosphorylcholines containing the combination of a C18:0 fatty acid unit and a C22:6 fatty acid unit. The mass-to-charge ratio (m/z) of the ionised spezies is 834.6 Da (+/−0.3 Da). A preferred fragmentation pattern is shown in FIG. 1 below.

The expression "method for diagnosing" as referred to in accordance with the present invention means that the method either essentially consists of the aforementioned steps or may include further steps. However, it is to be understood that the method, in a preferred embodiment, is a method carried out ex vivo, i.e. not practised on the human or animal body. Diagnosing as used herein refers to assessing the probability according to which a subject is suffering from a disorder. As will be understood by those skilled in the art, such an assessment, although preferred to be, may usually not be correct for 100% of the subjects to be diagnosed. The term, however, requires that a statistically significant portion of subjects can be identified as suffering from the disorder or as having a predisposition therefor. Whether a portion is statistically significant can be determined without further ado by the person skilled in the art using various well known statistic evaluation tools, e.g., determination of confidence intervals, p-value determination, WELCH test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, at least 95%. The p-values are, preferably, 0.2, 0.1, 0.05.

Diagnosing according to the present invention includes monitoring, confirmation, and classification of the relevant disorder or its symptoms. Monitoring relates to keeping track of an already diagnosed disorder, e.g. to analyze the progression of the disorder, the influence of a particular treatment on the progression of the disorder. Confirmation relates to the strengthening or substantiating a diagnosis already performed using other indicators or markers.

Classification relates to allocating the diagnosis according to the strength or kind of symptoms into different classes. Some of the conditions which appear in connection with increased peroxisomal proliferation may be accompanied by further metabolic changes.

The term "peroxisomal proliferation" or "increased peroxisomal proliferation" as used herein relates to a significantly increased number of peroxisomes which are formed in a cell or to a significantly increased peroxisomal activity found in a cell or both. Increased peroxisomal proliferation results in an impaired oxidative stress in the cell and, thus, in an increased predisposition for mutagenesis or cell death as well as other cellular disorders associated with an imbalanced ratio of radical oxidative molecular species and antioxidants. Preferably, induced peroxisomal proliferation as used herein results in a predisposition for cancer and for diseases selected from thyroid disorders, reproductive dysfunction, skeletal and cardiac myopathies, or dysfunction of the immune system. The symptoms and clinical signs of the aforementioned manifestations of increased peroxisomal proliferation are well known to the person skilled in the art and are described in detail in H. Marquardt, S. G. Schäfer, R. O. McClellan, F. Welsch (eds.), "Toxicology", Chapter 13: The Liver, 1999, Academic Press, London.

Each of the analytes to be determined in the method of the present invention is also suitable for diagnosing the diseases or disorders referred to herein when analysed alone. However, it was found in accordance with the present invention that a combination of at least five different analytes further strengthen the diagnosis since each of the analytes is an apparently statistically independent predictor of equal value for the diagnosis. Moreover, the specificity for liver toxicity is also significantly increased since influences from other tissues on the marker abundance are counterbalanced. Preferred marker combinations for specific liver enzyme inducing compound classes are those found in Table 1 and 2, below.

It is to be understood that in addition to a group consisting of at least five of the aforementioned analytes, additional analytes are, preferably, determined in the method of the present invention. The additional analytes are, preferably, also selected from the aforementioned group. In other words, preferably, at least six, at least seven, at least eight, at least nine, at least ten or all of the analytes of the aforementioned group are determined in the method of the present invention. The additional determination of these analytes even further strengthen the result obtained by the method of this invention. Furthermore, other analytes or metabolites (i.e. metabolites not specifically recited in the aforementioned group) or biomarkers, such as enzymes, may still be determined in addition.

In a particular preferred embodiment, the at least one analyte in the male sample is selected from the group consisting of: Coenzyme Q10, 16-Methylheptadecanoic acid, 17-Methyloctadecanoic acid, Eicosatrienoic acid (C20:3), and trans-4-Hydroxyproline. In an even more preferred embodiments, all of the aforementioned analytes are determined.

However, it is also preferably envisaged that in a group of at least five analytes to be determined in accordance with the present invention, one, two, three, or four analytes are from the aforementioned group of preferred analytes while the remaining analytes are analytes for male samples as specified elsewhere herein.

Thus, if the first analyte of a preferred group of five analytes to be determined in accordance with the present invention is Coenzyme Q10, the remaining four analytes are selected from a group consisting of the following analytes: 16-Methylheptadecanoic acid, 17-Methyloctadecanoic acid, Eicosatrienoic acid (C20:3), Threonine, Proline, Tyrosine, and trans-4-Hydroxyproline.

If the first and second analyte are Coenzym Q10 and 16-Methylheptadecanoic acid, the remaining three analytes are selected from a group consisting of: 17-Methyloctadecanoic acid, Eicosatrienoic acid (C20:3), Threonine, Proline, Tyrosine, and trans-4-Hydroxyproline.

If the first, second and third analytes are Coenzyme Q10, 16-Methylheptadecanoic acid, 17-Methyloctadecanoic acid, the remaining two analytes are selected from a group consisting of: Eicosatrienoic acid (C20:3), Threonine, Proline, Tyrosine, and trans-4-Hydroxyproline.

If the first, second, third and fourth analytes are Coenzyme Q10, 16-Methylheptadecanoic acid, 17-Methyloctadecanoic acid, Eicosatrienoic acid (C20:3), the remaining analyte is selected from a group consisting of: Threonine, Proline, Tyrosine, and trans-4-Hydroxyproline.

In a particular preferred embodiment, the at least one analyte in the female is selected from the group consisting of: Pantothenic acid, Glycerol, Linoleic acid (C18:cis[9,12]2), 16-Methylheptadecanoic acid, Cytosine, and Phosphatidylcholine (C18:0/C22:6). In an even more preferred embodiments, all six of the aforementioned analytes are determined. However, it is preferably envisaged that in a group of at least five analytes to be determined in accordance with the present invention, one, two, three, or four analytes are from the aforementioned group of preferred analytes while the remaining analytes are analytes for female samples as specified elsewhere herein.

However, it is also preferably envisaged that in a group of at least five analytes to be determined in accordance with the present invention, one, two, three, or four analytes are from the aforementioned group of preferred analytes while the remaining analytes are analytes for male samples as specified elsewhere herein.

Thus, if the first analyte of a preferred group of five analytes to be determined in accordance with the present invention is Pantothenic acid, the remaining four analytes are selected from a group consisting of the following analytes: Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6).

If the first and second analyte are Pantothenic acid and Glycerol, the remaining three analytes are selected from a group consisting of: Coenzyme Q9, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6).

If the first, second and third analytes are Pantothenic acid, Glycerol, and Linoleic acid (C18:cis[9,12]2), the remaining two analytes are selected from a group consisting of: Coenzyme Q9, Palmitic acid (C16:0), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6).

If the first, second, third and fourth analytes are Pantothenic acid, Glycerol, Linoleic acid (C18:cis[9,12]2), 16-Methylheptadecanoic acid, the remaining analyte is selected from a group consisting of: Coenzyme Q9, Palmitic acid (C16:0), 14-Methylhexadecanoic acid, gamma-Linolenic acid (C18:cis[6,9,12]3), Threonic acid, Cytosine, Phosphatidylcholine (C18:0/C22:6).

Analyte as used herein refers to at least one molecule of a specific analyte up to a plurality of molecules of the said specific analyte. It is to be understood further that a group of analytes means a plurality of chemically different molecules wherein for each analyte at least one molecule up to a plurality of molecules may be present. An analyte in accordance with the present invention encompasses all classes of organic or inorganic chemical compounds including those being comprised by biological material such as organisms. Preferably, the analyte in accordance with the present invention is a small molecule compound. More preferably, in case a plurality of analytes is envisaged, it will be understood that each analyte represents a metabolite and that the plurality of metabolites represent a metabolome. The metabolome is the collection of metabolites being comprised by an organism, an organ, a tissue or a cell at a specific time and under specific conditions. The analyte may differ from the metabolite which is represented thereby due to chemical modifications arising as arising as a result of purification steps, GC derivatives or other modifications required for determination. However, the person skilled in the art will readily be able to allocate the analyte to a metabolite or class of metabolites.

Metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, glycolysis, gluconeogenesis, hexose monophosphate pathway, oxidative pentose phosphate pathway, production and p-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, hormones, vitamins, cofactors such as prosthetic groups or electron carriers, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da.

Analytes as referred to in accordance with this invention are molecular species which are derived from the naturally occurring metabolite due to the purification and/or determination process. In some cases, the analyte will be identical. In other cases, however, it will be a chemical derivative thereof. Nevertheless, it is to be understood that the appearing of the analyte inevitably allows drawing conclusions on the occurrence of the metabolite.

The term "test sample" as used herein refers to samples to be used for the diagnosis of increased peroxisomal proliferation by the method of the present invention. Said test sample is a biological sample. Samples from biological sources (i.e. biological samples) usually comprise a plurality of metabolites. Preferred biological samples to be used in the method of the present invention are samples from body fluids, preferably, blood, plasma, serum, saliva, bile, urine or cerebrospinal fluid, or samples derived, e.g., by biopsy, from cells, tissues or organs, preferably from the liver. More preferably, the sample is a blood, plasma or serum sample, most preferably, a plasma sample. Biological samples are derived from a subject as specified elsewhere herein. Techniques for obtaining the aforementioned different types of biological samples are well known in the art. For example, blood samples may be obtained by blood taking while tissue or organ samples are to be obtained, e.g., by biopsy.

The aforementioned samples are, preferably, pre-treated before they are used for the method of the present invention. As described in more detail below, said pre-treatment may include treatments required to release or separate the compounds or to remove excessive material or waste. Suitable techniques comprise centrifugation, extraction, fractioning, ultrafiltration, protein precipitation followed by filtration and purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art.

Pre-treated samples as described before are also comprised by the term "sample" as used in accordance with the present invention.

The term "subject" as used herein relates to animals, preferably to mammals such as mice, rats, guinea pigs, rabbits, hamsters, pigs, sheep, dogs, cats, horses, monkeys, or cows and, also preferably, to humans. More preferably, the subject is a rodent and, most preferably, a rat. Other animals which may be diagnosed applying the method of the present invention are fishes, birds or reptiles. Preferably, said subject was in or has been brought into contact with a compound suspected to be capable of inducing increased peroxisomal proliferation. A subject which has been brought into contact with a compound suspected to induce increased peroxisomal proliferation may, e.g., be a laboratory animal such as a rat which is used in a screening assay for, e.g., toxicity of compounds. A subject suspected to have been in contact with a compound capable of inducing increased peroxisomal proliferation may be also a subject to be diagnosed for selecting a suitable therapy. Preferably, a compound capable of inducing increased peroxisomal proliferation as used herein is Benzylbutyl Phthalate, Fenofibrate, Clofibrate, Fenoforbrate, Diethylhexylphthalate or Wy 14643.

The term "determining the amount" as used herein refers to determining at least one characteristic feature of each analyte of the said at least five analytes. Characteristic features in accordance with the present invention are features which characterize the physical and/or chemical properties including biochemical properties of a analyte. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a analyte by standard operations, e.g., mathematical calculations such as multiplication, division or logarithmic calculus. Most preferably, the at least one characteristic feature allows the determination and/or chemical identification of the analyte and its amount. Accordingly, the characteristic value, preferably, also comprises information relating to the abundance of the metabolite from which the characteristic value is derived. For example, a characteristic value of a metabolite may be a peak in a mass spectrum. Such a peak contains characteristic information of the metabolite, i.e. the m/z (mass to charge ratio) information, as well as an intensity value being related to the abundance of the said analyte (i.e. its amount) in the sample.

As discussed before, each analyte of the group of analytes to be determined in accordance with the method of the present invention may be, preferably, determined quantitatively or semi-quantitatively. For quantitative determination, either the absolute or precise amount of the metabolite will be determined or the relative amount of the analyte will be determined based on the value determined for the characteristic feature(s) referred to herein above. The relative amount may be determined in a case were the precise amount of a analyte can or shall not be determined. In said case, it can be determined whether the amount in which the analyte is present is enlarged or diminished with respect to a second sample comprising said metabolite in a second amount. Quantitatively analysing a analyte, thus, also includes what is sometimes referred to as semi-quantitative analysis of a analyte.

Moreover, determining as used in the method of the present invention, preferably, includes using a compound separation step prior to the analysis step referred to before. Preferably, said compound separation step yields a time resolved separation of the analytes comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention. Suitable devices for such determination of metabolites are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference. As an alternative or in addition to mass spectrometry techniques, the following techniques may be used for compound determination: nuclear magnetic resonance (NMR), magnetic resonance imaging (MRI), Fourier transform infrared analysis (FT-IR), ultraviolet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado. The method of the present invention shall be, preferably, assisted by automation. For example, sample processing or pre-treatment can be automated by robotics. Data processing and comparison is, preferably, assisted by suitable computer programs and databases. Automation as described herein before allows using the method of the present invention in high-throughput approaches.

Moreover, the analyte can also be determined by a specific chemical or biological assay. Said assay shall comprise means which allow for specifically detecting the analyte in the sample. Preferably, said means are capable of specifically recognizing the chemical structure of the analyte or are capable of specifically identifying the analyte based on its capability to react with other compounds or its capability to elicit a response in a biological read out system (e.g., induction of a reporter gene). Means which are capable of specifically recognizing the chemical structure of a metabolite are, preferably, antibodies or other proteins which specifically interact with chemical structures, such as receptors or enzymes. Specific antibodies, for instance, may be obtained using the metabolite as antigen by methods well known in the art. Antibodies as referred to herein include both polyclonal and monoclonal antibodies, as well as fragments thereof, such as Fv, Fab and $F(ab)_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the metabolite are, preferably, enzymes which are involved in the metabolic conversion of the said metabolite. Said enzymes may either use the metabolite as a substrate or may convert a substrate into the metabolite. Moreover, said antibodies may be used as a basis to generate oligopeptides which specifically recognize the metabolite. These oligopeptides shall, for example, comprise the enzyme's binding domains or pockets for the said metabolite. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the metabolite may also be identified based on its capability to react with other compounds, i.e. by a specific chemical reaction. Further, the metabolite may be determined in a sample due to its capability to elicit a response in a biological read out system. The biological response shall be detected as read out indicating the presence and/or the amount of the metabolite comprised by the sample. The biological response may be, e.g., the induction of gene expression or a phenotypic response of a cell or an organism.

The term "reference" refers to values of characteristic features of each of the analytes of the group of analytes which can be correlated to increased peroxisomal proliferation. Such reference results are, preferably, obtained from a sample derived from a subject which has been brought into contact with Benzylbutyl Phthalate, Fenofibrate, Clofibrate, Fenoforbrate, Diethylhexylphthalate or Wy 14643. A subject may be brought into contact with the said compounds by each topic or systemic administration mode as long as the compounds are bioavailable. The reference results may be determined as described hereinabove for the amounts of the analytes. Alternatively, but nevertheless also preferred, the reference results may be obtained from sample derived from a subject which has not been brought into contact with Benzylbutyl Phthalate, Fenofibrate, Clofibrate, Fenoforbrate, Diethylhexylphthalate or Wy 14643 or a healthy subject with respect to increased peroxisomal proliferation and, more preferably, other diseases as well. Moreover, the reference, also preferably, could be a calculated reference, most preferably the average or median, for the relative or absolute amount for each of the analytes of the group of analytes derived from a population of individuals comprising the subject to be investigated. However, it is to be understood that the population of subjects to be investigated for determining a calculated reference, preferably, either consist of apparently healthy subjects (e.g. untreated) or comprise a number of apparently healthy subjects which is large enough to be statistically resistant against significant average or median changes due to the presence of the test subject(s) in the said population. The absolute or relative amounts of the analytes of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

More preferably, the reference results, i.e. values for at least one characteristic features of the analyte, will be stored in a suitable data storage medium such as a database and are, thus, also available for future diagnoses. This also allows efficiently diagnosing predisposition for a disease because suitable reference results can be identified in the database once it has been confirmed (in the future) that the subject from which the corresponding reference sample was obtained (indeed) showed increased peroxisomal proliferation.

The term "comparing" refers to assessing whether the results of the determination described hereinabove in detail, i.e. the results of the qualitative or quantitative determination of a analyte, are identical or similar to reference results or differ therefrom.

In case the reference results are obtained from a sample derived from a subject which has been brought into contact with Benzylbutyl Phthalate, Fenofibrate, Clofibrate, Fenoforbrate, Diethylhexylphthalate or Wy 14643, increased peroxisomal proliferation can be diagnosed based on the degree of identity or similarity between the test results obtained from the test sample and the aforementioned reference results, i.e. based on an identical or similar qualitative or quantitative composition with respect to the aforementioned analytes. The results of the test sample and the reference results are identical, if the values for the characteristic features and, in the case of quantitative determination, the intensity values are identical. Said results are similar, if the values of the characteristic features are identical but the intensity values are different. Such a difference is, preferably, not significant and shall be characterized in that the values for the intensity are within at least the interval between $1^{st}$ and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value the $50^{th}$, $60^{th}$, $70^{th}$, $80^{th}$, $90^{th}$ or $90^{th}$ percentile of the reference value.

In case the reference results are obtained a subject which has not been brought into contact with Benzylbutyl Phthalate, Fenofibrate, Clofibrate, Fenoforbrate, Diethylhexylphthalate or Wy 14643, increased peroxisomal proliferation can be diagnosed based on the differences between the test results obtained from the test sample and the aforementioned reference results, i.e. differences in the qualitative or quantitative composition with respect to the aforementioned analytes. The same applies if a calculated reference as specified above is used. The difference may be an increase in the absolute or relative amount of an analyte (sometimes referred to as up-regulation of the metabolite; see also Examples) or a decrease in either of said amounts or the absence of a detectable amount of the analyte (sometimes referred to as up-regulation of the metabolite; see also Examples). Preferably, the difference in the relative or absolute amount is significant, i.e. outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, $1^{st}$ and $99^{th}$ percentile of the reference value.

Preferably, the amounts of the analytes in comparison to the reference differ as follows:

(i) in a sample of a male: Coenzyme Q10 decreased, 16-Methylheptadecanoic acid decreased, 17-Methyloctadecanoic acid decreased, Eicosatrienoic acid (C20:3) increased, Threonine decreased, Proline decreased, Tyrosine decreased, trans-4-Hydroxyproline decreased; and (ii) in a sample of a female subject: Pantothenic acid increased, Coenzyme Q9 increased, Glycerol increased, Palmitic acid (C16:0) increased, Linoleic acid (C18:cis[9,12]2) increased, 14-Methylhexadecanoic acid increased, gamma-Linolenic acid (C18:cis[6,9,12]3) decreased, 16-Methylheptadecanoic acid decreased, Threonic acid increased, Cytosine decreased, Phosphatidylcholine (C18:0/C22:6) decreased. For the specific analytes referred to in this specification, preferred values for the changes in the relative amounts (i.e. "fold"-changes) or the kind of change (i.e. "up"- or "down"-regulation resulting in a higher or lower relative and/or absolute amount) are indicated in the Examples below.

The comparison is, preferably, assisted by automation. For example, a suitable computer program comprising algorithm for the comparison of two different data sets (e.g., data sets comprising the values of the characteristic feature(s)) may be used. Such computer programs and algorithm are well known in the art. Notwithstanding the above, a comparison can also be carried out manually.

The aforementioned methods for the determination of the analytes can be implemented into a device. A device as used herein shall comprise at least the aforementioned means. Moreover, the device, preferably, further comprises means for comparison and evaluation of the detected characteristic feature(s) of the analytes and, also preferably, the determined signal intensity. The means of the device are, preferably, operatively linked to each other. How to link the means in an operating manner will depend on the type of means included into the device. For example, where means for automatically qualitatively or quantitatively determining the metabolite are applied, the data obtained by said automatically operating means can be processed by, e.g., a computer program in order to facilitate the diagnosis. Preferably, the means are comprised by a single device in such a case. Said device may accordingly include an analyzing unit for the analytes and a computer unit for processing the resulting data for the diagnosis. Alternatively, where means such as test stripes are used for determining the analytes, the means for diagnosing may comprise control stripes or tables allocating the determined result data to result data known to be accompanied with increased peroxisomal proliferation or those being indicative for a healthy subject as discussed above. Preferred devices are those which can be applied without the particular knowledge of a specialized clinician, e.g., test stripes or electronic devices which merely require loading with a sample.

Alternatively, the methods for the determination of the analytes can be implemented into a system comprising several devices which are, preferably, operatively linked to each other. Specifically, the means must be linked in a manner as to allow carrying out the method of the present invention as described in detail above. Therefore, operatively linked, as used herein, preferably, means functionally linked. Depending on the means to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via LAN (Wireless LAN, W-LAN). A preferred system comprises means for determining analytes. Means for determining analytes as used herein encompass means for separating analytes, such as chromatographic devices, and means for analyte determination, such as mass spectrometry devices. Suitable devices have been described in detail above. Preferred means for compound separation to be used in the system of the present invention include chromatographic devices, more preferably devices for liquid chromatography, HPLC, and/or gas chromatography. Preferred devices for compound determination comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF. The separation and determination means are, preferably, coupled to each other. Most preferably, LC-MS and/or GC-MS is used in the system of the present invention as described in detail elsewhere in the specification. Further comprised shall be means for comparing and/or analyzing the results obtained from the means for determination of analytes. The means for comparing and/or analyzing the results may comprise at least one databases and an implemented computer program for comparison of the results. Preferred embodiments of the aforementioned systems and devices are also described in detail below.

Advantageously, it has been found in the study underlying the present invention that the amounts of a group of at least five of the aforementioned analytes serve as biomarkers for increased peroxisomal proliferation, in particular those peroxisomal proliferation induced by the peroxisomal proliferators Benzylbutyl Phthalate, Fenofibrate, Clofibrate, Fenoforbrate, Diethylhexylphthalate or Wy 14643. The specificity and accuracy of the method will be even more improved by determining all of the aformetioned analytes. A change in the quantitative and/or qualitative composition of the metabolome with respect to these specific analytes is indicative for increased peroxisomal proliferation. The morphological, physiological as well as biochemical parameters which are currently used for diagnosing peroxisomal proliferation are less specific and less sensitive in comparison to the biomarker determination provided by the present invention. Thanks to the present invention, the capability of a compound to induce peroxisomal proliferation, i.e. to be a so called "peroxisomal proliferators", can be more efficiently and reliably assessed. Moreover, based on the aforementioned findings, screening assays for drugs which ameliorate or inhibit increased peroxisomal proliferation are feasible. Furthermore, chemical compounds which, amongst other effects, induce peroxisomal proliferation and have lipid lowering properties are compounds such as MCPA (methyl-chloro-phenoxy-aceticacid), Dichlorprop (dichloro-phenoxy-proionicacid) and Mecoprop (methyl-chloro-phenoxy-aceticacid). They can also be identiefied by the method of the present invention.

The present invention, in principle, relates to the use of at least one, preferably, at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline or means for the detection thereof for the manufacture of a diagnostic device or composition for diagnosing increased peroxisomal proliferation in a male subject or at least one, preferably, at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6) or means for the detection thereof for the manufacture of a diagnostic device or composition for diagnosing increased peroxisomal proliferation in a female subject.

All definitions and explanations of the terms made above apply mutatis mutandis for the aforementioned methods and all other embodiments described further below except stated otherwise in the following.

It follows from the above that the present invention also contemplates a method of determining whether a compound is capable of inducing increased peroxisomal proliferation in a subject comprising:

(a) determining in a sample of a male subject which has been brought into contact with a compound suspected to be capable of inducing increased peroxisomal proliferation the amount of at least one, preferably, at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline or in a test sample of a female which has been brought into contact with a compound suspected to be capable of inducing increased peroxisomal proliferation at least one, preferably, at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6); and (b) comparing the amounts determined in step (a) to a reference, whereby the capability of the compound to induce increased peroxisomal proliferation is determined.

In a preferred embodiment of said method, said compound is at least one compound selected from the group consisting of: Benzylbutyl Phthalate, Fenofibrate, Clofibrate, Fenoforbrate, Diethylhexylphthalate or Wy 14643.

Preferably, said reference is derived from a subject which suffers from increased peroxisomal proliferation or from a subject which has been brought into contact with at least one compound selected from the group consisting of: Benzylbutyl Phthalate, Fenofibrate, Clofibrate, Fenoforbrate, Diethylhexylphthalate or Wy 14643. More preferably, essentially identical amounts for the analytes in the test sample and the reference are indicative for increased peroxisomal proliferation.

Also preferably, said reference is derived from a subject known to not suffer from increased peroxisomal proliferation or from a subject which has not been brought into contact with at least one compound selected from the group consisting of: Benzylbutyl Phthalate, Fenofibrate, Clofibrate, Fenoforbrate, Diethylhexylphthalate or Wy 14643. Alternatively, but also preferred, the said reference is a calculated reference for the analytes for a population of subjects. More preferably, amounts for the analytes which differ in the test sample in comparison to the reference are indicative for increased peroxisomal proliferation.

Preferred indicative amounts for increased peroxisomal proliferation are disclosed elsewhere in this specification.

The present invention also relates to a method of identifying a substance for treating increased peroxisomal proliferation comprising the steps of:

(a) determining in a sample of a male subject suffering from increased peroxisomal proliferation which has been brought into contact with a candidate substance suspected to be capable of treating increased peroxisomal proliferation the amount of at least one, preferably, at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline or in a sample of a female subject suffering from increased peroxisomal proliferation which has been brought into contact with a candidate substance suspected to be capable of treating increased peroxisomal proliferation the amount of at least one, preferably, at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6); and (b) comparing the amounts determined in step (a) to a reference, whereby a substance capable of treating increased peroxisomal proliferation is to be identified.

Specifically, in case of the method of identifying a substance useful for treating increased peroxisomal proliferation, said reference is, preferably, derived from a subject which has been brought into contact with at least one compound selected from the group consisting of: Benzylbutyl Phthalate, Fenofibrate, Clofibrate, Fenoforbrate, Diethylhexylphthalate or Wy 14643 or a subject which suffers from increased peroxisomal proliferation. More preferably, amounts for the metabolites which differ in the test sample and the reference are indicative for a substance useful for treating increased peroxisomal proliferation.

Specifically, indicative for a substance capable of treating increased peroxisomal proliferation are amounts of the analytes in comparison to the reference which differ as follows: (i) in a sample of a male: Coenzyme Q10 increased, 16-Methylheptadecanoic acid increased, 17-Methyloctadecanoic acid increased, Eicosatrienoic acid (C20:3) decreased, Threonine decreased, Proline increased, Tyrosine increased, trans-4-Hydroxyproline increased and (ii) in a sample of a female subject: Pantothenic acid decreased, Coenzyme Q9 decreased, Glycerol decreased, Palmitic acid (C16:0) decreased, Linoleic acid (C18:cis[9,12]2) decreased, 14-Methylhexadecanoic acid decreased, gamma-Linolenic acid (C18:cis[6,9,12]3) increased, 16-Methylheptadecanoic acid increased, Threonic acid decreased, Cytosine increased, Phosphatidylcholine (C18:0/C22:6) increased.

Alternatively, the said reference may be, preferably, be derived from a subject which has not been brought into contact with Benzylbutyl Phthalate, Fenofibrate, Clofibrate, Fenoforbrate, Diethylhexylphthalate or Wy 14643 or a subject known to not suffer from increased peroxisomal proliferation or may be a calculated reference for the analytes in a population of subjects. If such a reference is used, identical or similar amounts for the metabolites in the test sample and the reference are indicative for a substance useful for treating increased peroxisomal proliferation.

The term "substance for treating increased peroxisomal proliferation" refers to compounds which may directly interfere with the biological mechanisms inducing increased peroxisomal proliferation referred to elsewhere in this specification. Substances to be identified by the method of the present invention may be organic and inorganic chemicals, such as small molecules, polynucleotides, oligonucleotides, peptides, polypeptides including antibodies or other artificial or biological polymers. Preferably, the substances are suitable as drugs, pro-drugs or lead substances for the development of drugs or pro-drugs.

It is to be understood that if the methods of the present invention are to be used for identifying drugs for the therapy of increased peroxisomal proliferation or for toxicological assessments of compounds (i.e. determining whether a compound is capable of inducing increased peroxisomal proliferation), test samples of a plurality of subjects may be investigated for statistical reasons. Preferably, the metabolome within such a cohort of test subjects shall be as similar as possible in order to avoid differences which are caused, e.g., by factors other than the compound to be investigated. Subjects to be used for the said methods are, preferably, laboratory animals such as rodents and more preferably rats. It is to be understood further that the said laboratory animals shall be, preferably, sacrificed after completion of the method of the present invention. All subjects of a cohort test and reference animals shall be kept under identical conditions to avoid any differential environmental influences. Suitable conditions and methods of providing such animals are described in detail in WO2007/014825. Said conditions are hereby incorporated by reference.

The present invention also relates to a data collection comprising characteristic values for the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline and/or at least the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6).

The term "data collection" refers to a collection of data which may be physically and/or logically grouped together. Accordingly, the data collection may be implemented in a single data storage medium or in physically separated data storage media being operatively linked to each other. Preferably, the data collection is implemented by means of a database. Thus, a database as used herein comprises the data collection on a suitable storage medium. Moreover, the database, preferably, further comprises a database management system. The database management system is, preferably, a network-based, hierarchical or object-oriented database management system. Furthermore, the database may be a federal or integrated database. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative for increased peroxisomal proliferation (e.g. a query search). Thus, if an identical or similar data set can be identified in the data collection, the test data set will be associated with increased peroxisomal proliferation. Consequently, the information obtained from the data collection can be used to diagnose increased peroxisomal proliferation based on a test data set obtained from a subject.

Moreover, the present invention pertains to a data storage medium comprising the said data collection.

The term "data storage medium" as used herein encompasses data storage media which are based on single physical entities such as a CD, a CD-ROM, a hard disk, optical storage media, or a diskette. Moreover, the term further includes data storage media consisting of physically separated entities which are operatively linked to each other in a manner as to provide the aforementioned data collection, preferably, in a suitable way for a query search.

The present invention also relates to a system comprising
(a) means for comparing characteristic values of metabolites of a sample operatively linked to
(b) the data storage medium of the present invention.

The term "system" as used herein relates to different means which are operatively linked to each other. Said means may be implemented in a single device or may be implemented in physically separated devices which are operatively linked to each other. The means for comparing characteristic values of analytes operate, preferably, based on an algorithm for comparison as mentioned before. The data storage medium, preferably, comprises the aforementioned data collection or database, wherein each of the stored data sets being indicative for increased peroxisomal proliferation. Thus, the system of the present invention allows identifying whether a test data set is comprised by the data collection stored in the data storage medium. Consequently, the system of the present invention may be applied as a diagnostic means in diagnosing increased peroxisomal proliferation.

In a preferred embodiment of the system, means for determining characteristic values of metabolites of a sample are comprised.

The term "means for determining characteristic values of metabolites" preferably relates to the aforementioned devices for the determination of analytes such as mass spectrometry devices, NMR devices or devices for carrying out chemical or biological assays for the analytes.

The present invention also encompasses a diagnostic composition comprising at least one, preferably, at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline and/or at least one, preferably, at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6) or means for the determination thereof.

Further encompassed is a diagnostic device comprising
(a) means for determining characteristic values of at least one, preferably, at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline and/or at least one, preferably, at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6); and
(b) means for diagnosing liver toxicicty based on the characteristic values determined by the means of (a).

The term "diagnostic means", preferably, relates to a diagnostic device, system or biological or chemical assay as specified elsewhere in the description in detail.

The expression "means for determining characteristic values of a group of metabolites" refers to devices or agents which are capable of specifically recognizing the metabolite(s). Suitable devices may be spectrometric devices such as mass spectrometry, NMR devices or devices for carrying out chemical or biological assays for the metabolites. Suitable agents may be compounds which specifically detect the metabolites. Detection as used herein may be a two-step process, i.e. the compound may first bind specifically to the metabolite to be detected and subsequently generate a detectable signal, e.g., fluorescent signals, chemiluminescent signals, radioactive signals and the like. For the generation of the detectable signal, further compounds may be required which are all comprised by the term "means for determining characteristic values of a group of metabolites". Compounds which specifically bind to the metabolite are described elsewhere in the specification in detail and include, preferably, enzymes, antibodies, ligands, receptors or other biological molecules or chemicals which specifically bind to the metabolites.

All references referred to above are herewith incorporated by reference with respect to their entire disclosure content as well as their specific disclosure content explicitly referred to in the above description.

Figure 1:
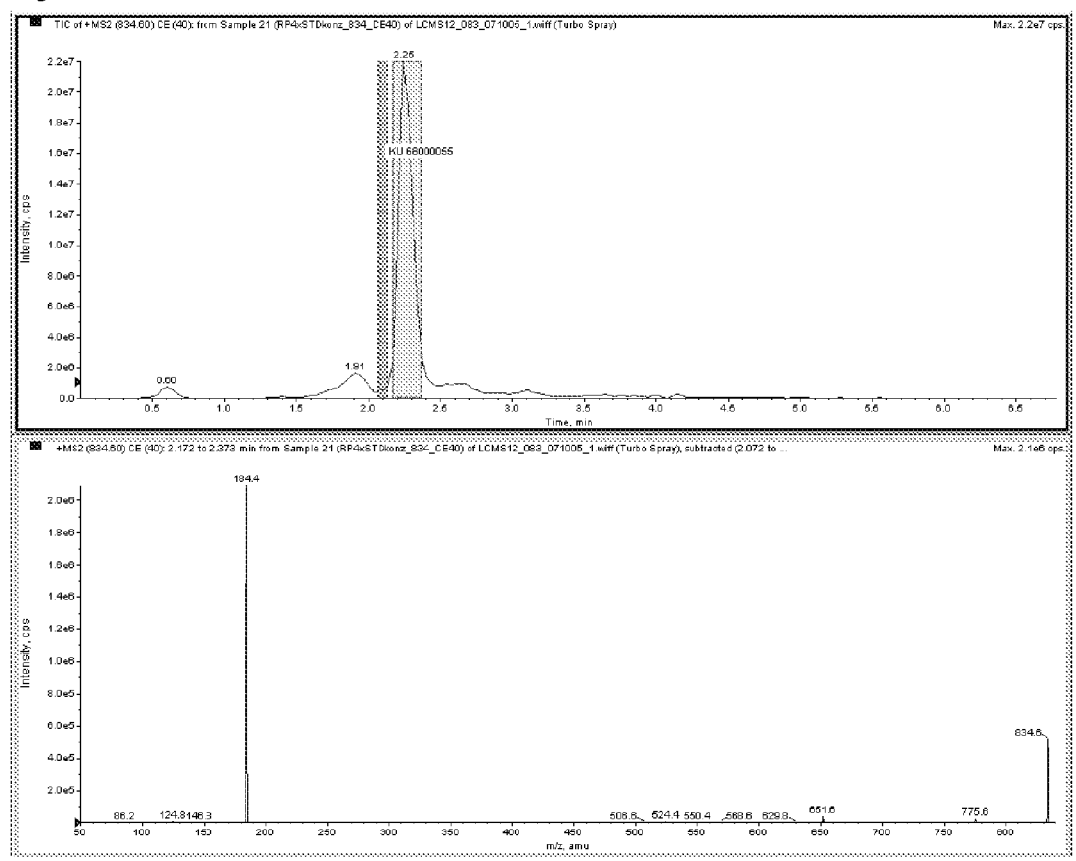
FIGS. 1 and 1a show a fragmentation pattern of Phosphatidyleholine (C18:0/C22:6).
Figure 1A:
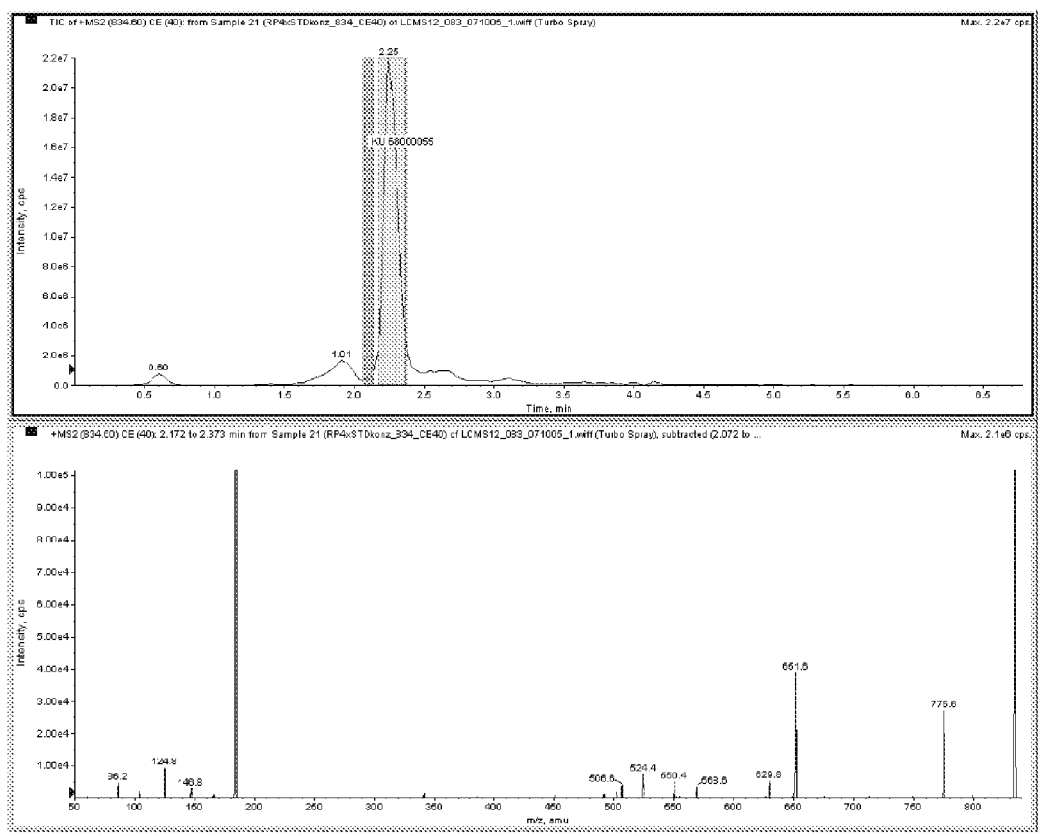

The following Examples are merely for the purposes of illustrating the present invention. They shall not be construed, whatsoever, to limit the scope of the invention in any respect.

EXAMPLE

Biomarkers Associated with Increased Peroxisomal Proliferation

A group of each 5 male and female rats was dosed once daily with the indicated compounds (see tables below) at 10 and 100 mg/kg body weight per gavage over 28 days. Additional groups of each 5 male and female animals served as controls. Before starting the treatment period, animals, which were 62-64 days old when supplied, were acclimatized to the housing and environmental conditions for 7 days. All animals of the animal population were kept under the same constant temperature (20-24±3° C.) and the same constant humidity (30-70%). Each animal of the animal population was kept in a separate cage. The animals of the animal population are fed ad libitum. The food to be used was be essentially free of chemical or microbial contaminants. Drinking water was also offered ad libitum. Accordingly, the water was be free of chemical and microbial contaminants as laid down in the European Drinking Water Directive 98/83/EG. The illumination period was 12 hours light followed by 12 hours darkness (12 hours light, from 6:00 to 18:00, and 12 hours darkness, from 18:00 to 6:00).

In the morning of day 7, 14, and 28, blood was taken from the retroorbital venous plexus from fasted anaesthetized animals. From each animal, 1 ml of blood was collected with EDTA as anticoagulant. The samples were be centrifuged for generation of plasma. All plasma samples were covered with a $N_2$ atmosphere and then stored at −80° C. until analysis.

For mass spectrometry-based metabolite profiling analyses plasma samples were extracted and a polar and a nonpolar fraction was obtained. For GC-MS analysis, the nonpolar fraction was tested with methanol under acidic conditions to yield the fatty acid methyl esters. Both fractions were further derivatised with O-methyl-hydroxyamine hydrochloride and pyridine to convert Oxo-groups to O-metyloximes and subsequently with a silyating agent before hydrolysis. In LC-MS analysis, both fractions were reconstituted in appropriate solvent mixtures. HPLC was performed by gradient elution on reversed phase separation columns. For mass spectrometric detection metanomics proprietary technology was applied which allows target and high sensitivity MRM (Multiple Reaction Monitoring) profiling in parallel to a full screen analysis.

Following comprehensive analytical validation steps, the data for each analyte were normalized against data from pool samples. These samples were run in parallel through the whole process to account for process variability. The significance of treatment group values specific for sex, dose group and metabolite was determined by comparing means of the treated groups to the means of the respective untreated control groups using Student's t-test. Normalized treatment group values and their significance were fed into a database for further statistics and data mining processes.

The changes of the group of plasma metabolites being indicative for increased peroxisomal proliferation after treatment of the rats are shown in the following tables:

TABLE 1

Markers for peroxisomal proliferators in male rats

| Metabolite | Direction | Benzylbutyl Phthalate (MOA6) | | | Clofibrate (MOA50) | | |
|---|---|---|---|---|---|---|---|
| | | mh7 | mh14 | mh28 | mh7 | mh14 | mh28 |
| Coenzyme Q10 | down | 0.51 | 0.34 | 0.27 | 0.45 | 0.60 | 0.47 |
| 16-Methyl-heptadecanoic acid | down | 0.24 | 0.31 | 0.20 | 0.24 | 0.21 | 0.28 |
| 17-Methyl-octadecanoic acid | down | 0.37 | 0.28 | 0.30 | 0.35 | 0.27 | 0.37 |
| Eicosatrienoic acid (C20:3) | up | 2.56 | 3.12 | 4.12 | 1.65 | 1.72 | 2.54 |
| Threonine | down | 0.55 | 0.69 | 0.81 | 0.68 | 1.02 | 1.06 |
| Proline | down | 0.74 | 0.85 | 0.84 | 0.78 | 0.80 | 0.87 |
| Tyrosine | down | 0.74 | 0.83 | 0.97 | 0.87 | 0.95 | 1.02 |
| trans-4-Hydroxy-proline | down | 0.69 | 0.65 | 0.83 | 0.77 | 0.64 | 0.57 |

TABLE 2

Markers for peroxisomal proliferators in female rats

| Metabolite | Direction | Benzylbutyl Phthalate (MOA6) | | | Clofibrate (MOA50) | | |
|---|---|---|---|---|---|---|---|
| | | fh7 | fh14 | fh28 | fh7 | fh14 | fh28 |
| Pantothenic acid | up | 1.82 | 2.06 | 2.42 | 1.07 | 1.75 | 1.22 |
| Coenzyme Q9 | up | 1.44 | 1.50 | 1.78 | 1.86 | 1.64 | 2.55 |
| Glycerol, lipid fraction | up | 1.15 | 1.48 | 2.43 | 1.39 | 1.64 | 4.99 |
| Palmitic acid (C16:0) | up | 1.48 | 1.79 | 1.94 | 1.05 | 1.38 | 2.31 |
| Gamma-Linolenic acid (C18:cis[6,9,12]3) | up | 1.98 | 1.64 | 2.08 | 2.04 | 1.88 | 7.00 |
| 16-Methyl-heptadecanoic acid | down | 0.55 | 0.66 | 0.85 | 0.55 | 0.75 | 0.75 |
| 17-Methyl-octadecanoic acid | down | 0.78 | 0.64 | 0.69 | 0.48 | 0.57 | 0.77 |
| Threonic acid | up | 1.20 | 1.53 | 1.74 | 1.23 | 1.30 | 1.30 |
| Cytosine | down | 0.77 | 0.63 | 0.79 | 0.87 | 0.86 | 1.00 |
| Phosphatidylcholine (C18:0/C22:6) | down | 0.59 | 0.86 | 0.81 | 0.88 | 0.71 | 0.53 |

The invention claimed is:

1. A method of determining whether a compound is capable of inducing increased peroxisomal proliferation in a subject comprising:
   (a) selecting a male or female subject brought into contact with a compound suspected to be capable of inducing increased peroxisomal proliferation;
   (b) obtaining a body fluid test sample from the male or female subject;
   (c) determining from the body fluid test sample from the male subject the amount of at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline, or determining from the body fluid test sample from the female subject the amount of at least five of the following analytes Pantothenic acid, Coenzyme Q9, Glycerol, Palmitic acid (C16:0), Linoleic acid (C18:cis [9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6);
   (d) comparing the amounts determined in step (c) to corresponding reference results, wherein the reference results comprise (i) reference results obtained from one or more samples derived from one or more subjects which has been brought into contact with Benzylbutyl Phthalate, Fenofibrate, Clofibrate, Fenoforbrate, Diethylhexylphthalate or Wy 14643, (ii) reference results obtained from one or more samples derived from one or more subjects which has not been brought into contact with Benzylbutyl Phthalate, Fenofibrate, Clofibrate, Fenoforbrate, Diethylhexylphthalate or Wy 14643, (iii) reference results obtained from one or more samples derived from one or more subjects which suffers from increased peroxisomal proliferation, or (iv) reference results obtained from one or more samples derived from one or more subjects known to not suffer from increased peroxisomal proliferation; and (e) based on the comparison of step (d), determining whether the compound is capable of inducing increased peroxisomal proliferation.

2. The method of claim 1, wherein said determining the amount of analytes comprises mass spectrometry.

3. The method of claim 2, wherein said mass spectrometry is liquid chromatography (LC)-MS or gas chromatography (GC)-MS.

4. The method of claim 3, wherein the method is automated.

5. The method of claim 4, wherein the method comprises computer assisted data processing.

6. The method of claim 1, further comprising identifying the compound which induces increased peroxisomal proliferation.

7. The method of claim 6, limiting industrial application of the compound which induces increased peroxisomal proliferation.

8. A method of identifying a substance for treating increased peroxisomal proliferation comprising the steps of:

(a) selecting a male or female subject suffering from increased peroxisomal proliferation which subject has been brought into contact with a candidate substance suspected to be capable of treating increased peroxisomal proliferation;

(b) obtaining a body fluid test sample from the male or female subject;

(c) determining from the body fluid test sample from the male subject the amount of at least five of the following analytes Coenzyme Q10, 16-Methylheptadecanoic acid, 17-Methyloctadecanoic acid, Eicosatrienoic acid (C20:3), Threonine, Proline, Tyrosine, trans-4-Hydroxyproline, or determining from the body fluid test sample from the female subject the amount of at least five of the following analytes Pantothenic acid, Coenzyme Q9, Glycerol, Palmitic acid (C16:0), Linoleic acid (C18:cis[9,12]2), 14-Methylhexadecanoic acid, gamma-Linolenic acid (C18:cis[6,9,12]3), 16-Methylheptadecanoic acid, Threonic acid, Cytosine, Phosphatidylcholine (C18:0/C22:6);

(d) comparing the amounts determined in step (c) to corresponding reference results, wherein the reference results comprise (i) reference results obtained from one or more samples derived from one or more subjects which has been brought into contact with Benzylbutyl Phthalate, Fenofibrate, Clofibrate, Fenoforbrate, Diethylhexylphthalate or Wy 14643, (ii) reference results obtained from one or more samples derived from one or more subjects which has not been brought into contact with Benzylbutyl Phthalate, Fenofibrate, Clofibrate, Fenoforbrate, Diethylhexylphthatate or Wy 14643, (iii) reference results obtained from one or more samples derived from one or more subjects which suffers from increased peroxisomal proliferation, or (iv) reference results obtained from one or more samples derived from one or more subjects known to not suffer from increased peroxisomal proliferation healthy subjects; and (e) based on the comparison of step (d), identifying and selecting the substance for treating increased peroxisomal proliferation in a subject in need thereof.

9. The method of claim 8, wherein said reference result is obtained from one or more samples derived from (i) one or more subjects which suffers from increased peroxisomal proliferation; or (ii) one or more subjects which has been brought into contact with at least one compound selected from the group consisting of: Benzylbutyl Phthalate, Fenofibrate, Clofibrate, Fenoforbrate, Diethylhexylphthalate, and Wy 14643.

10. The method of claim 9, wherein amounts for the analytes which differ in the body fluid test sample and the reference result are indicative for a substance capable of treating increased peroxisomal proliferation.

11. The method of claim 9, wherein indicative for a substance capable of treating increased peroxisomal proliferation are amounts of the analytes in comparison to the reference result which differ as follows: (i) in a body fluid sample of a male: Coenzyme Q10 increased, 16-Methylheptadecanoic acid increased, 17-Methyloctadecanoic acid increased, Eicosatrienoic acid (C20:3) decreased, Threonine increased, Proline increased, Tyrosine increased, trans-4-Hydroxyproline increased; and (ii) in a body fluid sample of a female subject: Pantothenic acid decreased, Coenzyme Q9 decreased, Glycerol decreased, Palmitic acid (C16:0) decreased, Linoleic acid (C18:cis[9,12]2) decreased, 14-Methylhexadecanoic acid decreased, gamma-Linolenic acid (C18:cis[6,9,12]3) increased, 16-Methylheptadecanoic acid increased, Threonic acid decreased, Cytosine increased, Phosphatidylcholine (C18:0/C22:6) increased.

12. The method of claim 8, wherein said reference result is obtained from one or more samples derived from (i) one or more subjects known to not suffer from increased peroxisomal proliferation; or (ii) one or more subjects which has not been brought into contact with at least one compound selected from the group consisting of: Benzylbutyl Phthalate, Fenofibrate, Clofibrate, Fenoforbrate, Diethylhexylphthalate, and Wy 14643.

13. The method of claim 12, wherein identical amounts for the analytes in the body fluid test sample and the reference result are indicative for a substance capable of treating increased peroxisomal proliferation.

14. The method of claim 8, wherein said determining the amount of analytes comprises mass spectrometry.

15. The method of claim 14, wherein said mass spectrometry is liquid chromatography (LC)-MS or gas chromatography (GC)-MS.

16. The method of claim 15, wherein the method is automated.

17. The method of claim 16, wherein the method comprises computer assisted data processing.

* * * * *